(12) United States Patent
Henck

(10) Patent No.: US 6,475,722 B1
(45) Date of Patent: Nov. 5, 2002

(54) SURFACE TREATMENTS FOR DNA PROCESSING DEVICES

(75) Inventor: Steven A. Henck, Woodbridge, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/192,605

(22) Filed: Nov. 16, 1998

Related U.S. Application Data

(60) Provisional application No. 60/067,387, filed on Dec. 3, 1997.

(51) Int. Cl.$^7$ .......................... C12Q 1/68; C12P 19/34; H01R 43/00; C07H 21/02; B01D 57/02
(52) U.S. Cl. ...................... 435/6; 435/91.2; 435/283.1; 435/285.2; 435/287.2; 204/450; 204/451; 204/454; 204/507; 29/825; 536/22.1; 536/23.1; 536/24.3; 536/24.31; 536/24.32; 536/24.33
(58) Field of Search ....................... 437/1, 78; 204/450, 204/451, 454, 507; 435/91.2, 283.1, 285.2, 287.2

(56) References Cited

U.S. PATENT DOCUMENTS

| | | | |
|---|---|---|---|
| 5,194,393 A | * | 3/1993 | Hugle et al. |
| 5,578,179 A | * | 11/1996 | Demorest et al. |
| 5,587,128 A | | 12/1996 | Wilding et al. ............... 422/50 |

FOREIGN PATENT DOCUMENTS

| | | |
|---|---|---|
| EP | 0 648 776 A1 | 4/1995 |
| JP | 07058198 | * 8/1995 |
| WO | PCT/US96/35810 | 11/1996 |
| WO | PCT/US97/36171 | 10/1997 |
| WO | WO 98/22625 | 5/1998 |

OTHER PUBLICATIONS

Thompson et al NAR vol. 18 No. 4 pp. 1074 1990.*
International Search Report for PCT/US 98/24506 (5 pages).
Adams, "Dielectric and polysilicon film deposition" In: VLSI Technology, Chapter 6. pp 233–271. Singapore, McGraw–Hill Book co. 1988.
Karymov, et al. "Fixation of DNA directly on optical waveguide surfaces for molecular probe biosensor development" *Sensors and Actuators B:chemical.* 29:324–327. 1995.
Kern and Puotinen. "Cleaning solutions based on hydrogen peroxide for use in silicon semiconductor technology." *RCA Review*, 31: 187–206. 1970.
Shoffner et al. "Chip PCR. I. Surface passivation of microfabricated silicon–glass chips for PCR." *Nucl Acids Res. 24*: 375–379.
Chevet, et al., "Low concentrations of tetramethylammonium chloride increase yield and specificity of PCR." *Nucleic Acids Research. 23*: 3343–3344, 1995.

De Gennes, "Wetting: statics and dynamics." *Rev Mod Phys. 57*: 827–863, 1985.
Drmanac, et al., "DNA sequence determination by hybridization: a strategy for efficient large–scale sequencing." *Science. 260*: 1649–52, 1993.
Henck, "Lubrication of digital micromirror devices." *Tribology Letters. 3*: 239–247, 1997.
Hjerten, "High performance electrophoresis elimination of electroendosmosis and solute adsorption." *J Chromatogr. 347*: 191–198, 1985.
Ju, "Fluorescent energy transfer dye–labeled primers for DNA sequencing and analysis." *Proc Nati Acad Sci USA. 92*: 4347–4351, 1995.
Lennon, et al., "Hybridization analyses of arrayed cDNA libraries." *Trends In Genetics. 7*: 314–317, 1991.
Liang, "Differential display of eukaryotic messenger RNA by means of the polymerase chain reaction." *Science. 257*: 967–971, 1992.
Liang, et al., "Recent advances in differential display," *Current Opinions in Immunology, 7*: 274–280, 1995.
Lisitsyn, et al., "Cloning the differences between two complex genomes." *Science. 259*: 946–50, 1993.
McClelland, et al., "Arbitrary primed PCR fingerprinting of RNA applied to mapping differentially expressed genes." *Exs. 67*: 103–15, 1993.
Mutter, et al., "PCR bias in amplification of androgen receptor alleles, a trinucleotide repeat marker used in clonality studies." *Nuc Acid Res. 23*: 1411–1418, 1995.
Prashar, "Analysis of Differential Gene Expression by Display of 3'–end Restriction Fragments of cDNAs." *Proc Nat Acad Sci USA. 93*: 659–663, 1996.
Welsh, et al., "Arbitrarily primed PCR fingerprinting of RNA." *Nucleic Acid Res. 20*: 4965–70, 1992.

* cited by examiner

Primary Examiner—Jeffrey Siew
(74) Attorney, Agent, or Firm—Ivor R. Elrifi; Mintz, Levin, Cohn, Ferris, Glovsky and Popeo, P.C.

(57) ABSTRACT

The present invention discloses methodologies for the treatment of the surface(s) of DNA processing devices so as to greatly reduce DNA adsorption to the surface(s) exposed to the DNA-containing media. These aforementioned surface treatments include: (i) the deposition of thin-films of silicon-rich, silicon nitride and of hydroxyl-containing,low-temperature silicon oxide and (ii) the washing of surface with a basic, oxidative wash solution. The present invention also discloses the fabrication of DNA processing devices utilizing surface(s) treated by the methods described above. Such DNA processing devices include, for example, miniaturized electrophoresis and other DNA separation devices, miniaturized PCR reactors, and the like. The present invention further discloses methodologies for testing the degree of DNA adherence to a given surface. Additionally, the methodologies and devices of the present invention are also applicable to the processing of nucleic acids, in generally.

31 Claims, 11 Drawing Sheets

| Surface | Emission (counts/s) |
|---|---|
| LPCVD Silicon Rich Nitride | 15255 |
| PECVD LTO | 28000 |
| LPCVD LTO | 33450 |
| Thermal Oxide | 67850 |
| Poly-Hexane | 121230 |
| Teflon AF | 180050 |
| Spin-on-Glass | 188230 |
| LPCVD Stoichiometric Nitride | 371550 |
| Photoresist | 2000000 |

Table 1

| Surface | HMDS + i-line PR | O$_2$ plasma Strip | PR-2000 Strip | NH$_4$OH H$_2$O$_2$ | Emission (counts/sec) |
|---|---|---|---|---|---|
| 1 | | | | | 67,850 |
| 2 | | | | X | 45,520 |
| 3 | X | X | | | 356,925 |
| 4 | X | X | | X | 25,384 |
| 5 | X | | X | | 96,620 |
| 6 | X | | X | X | 14,100 |

Table 2

|  | θ (H$_2$O) | θ (CH$_2$I$_2$) | θ (Hexadecane) | Emission (counts/sec) |
| --- | --- | --- | --- | --- |
| Surface 6 | 0 | 28 | 22 | 14,100 |
| LPCVD Silicon Rich Nitride | 33 | 38 | 0 | 15,255 |
| Surface 4 | 22 | 30 | 0 | 25,384 |
| PECVD LTO | 26 | 42 | 0 | 28,000 |
| LPCVD LTO | 34 | 42 | 0 | 33,450 |
| Surface 28 | 0 | 30 | 30 | 45,520 |
| Surface 1 (thermal oxide) | 22 | 30 | 25 | 67,850 |
| Surface 5 | 23 | 34 | 0 | 96,620 |
| Poly-Hexane | 75 | 70 | 0 | 121,230 |
| Teflon AF | 94 | 90 | 60 | 180,050 |
| Spin-on-Glass | 80 | 52 | 0 | 188,230 |
| Surface 3 | 0 | 26 | 0 | 356,925 |
| LPCVD Stoichiometric Nitride | 36 | 40 | 0 | 371,550 |
| Photoresist | 64 | 38 | 0 | 2,000,000 |

Table 3

SURFACE TREATMENTS FOR DNA PROCESSING DEVICES

This application is a provisional of No. 60/067,387 filed Dec. 3, 1997.

GRANT SUPPORT

The present invention was made with Government support under Grant number 70NANB7H3004 awarded by the Advanced Technology Program of the National Institute of Standards and Technology. The Government may, therefore, have certain rights in the invention.

FIELD OF THE INVENTION

The present invention relates to improved nucleic acid processing devices of all types, and more particularly to miniaturized DNA processing devices with surface treatments designed to reduce DNA adsorption to device surfaces exposed to DNA containing mediums.

BACKGROUND OF THE INVENTION

A recent development in the fields of analytical chemistry and biotechnologyhas been the miniaturization of devices and systems for the processing and analysis of DNA. See e.g., McCormick, et al., 1997. *Anal. Chem.* 69:2626. Similarly, the current trend towards microfabrication has been driven by efforts to parallel the miniaturization accomplished in the semiconductor industry, and to exploit similar microfabrication techniques. See e.g., Ramsey, et al., 1995. *Nature Med.* 1:1093. Justifications for miniaturization include reduced cost, increased speed and reliability, distributed access (point-of-care diagnostics), decreased sample and reagent consumption and reduced waste generation.

An example of a microfabricated DNA analysis device is set forth in PCT Publication WO 96/35810, which is hereby incorporated by reference in its entirely. This aforementioned publication describes electrophoresis devices for the separation and observation of biopolymer fragments in an electrophoretic gel. In one embodiment, an electrophores is device is disclosed which possesses miniaturized electrophores is lanes, which are formed by open channels in a flat plate having dimensions down to approximately 25 $\mu$m and closed by a flat cover plate. In a further embodiment, the publication discloses an electrophores is device which includes an integrally-associated, miniaturized reactor for generating biopolymer fragments for subsequent separation by the device. These miniaturized features are capable of being constructed by various micro-machining techniques, including the lithographic and etching methodologies initially developed in the semiconductor industry.

A further example of a microfabricated DNA analysis device is set forth in the commonly-assigned, U.S. patent application Ser. No. 08/623,346, filed Mar. 27, 1996, which is hereby incorporated by reference in its entirety. This aforementioned application discloses an apparatus for the separation of charged particles in a medium according to the differential diffusion properties of the particles within the electrophoretic medium by use of a spatially- and temporally-varying electric potential. Such an apparatus has application to the separation of single-stranded or double-stranded DNA fragments. In one embodiment, the device consists of a series of miniaturized electrodes which are patterned on a substrate and a cover plate which has one or more miniaturized channels (also down to approximately 25 $\mu$m). This device is also described as being fabricated using the techniques initially developed within the semiconductor industry.

Due to their decreased dimensions the ratio of surface to volume in miniaturized or microfabricated DNA processing devices is markedly increased over other conventional devices. See e.g., Shoffner, et al., 1996. *Nuc. Acids Res.* 24:375. This increased surface-to-volume ratio increases the significance of effects of surface chemistry in such microfabricated devices. In particular, it is well known in the art that DNA interacts strongly with and adheres to a number of surfaces. See e.g., Hjerten 1985. *J. Chromatography* 347:191. The hydrophilic phosphate groups and hydrophobic protonated bases mean that almost any surface is likely to interact. In addition, the harsh processes used during the standard microfabrication process can damage or contaminate the surfaces creating even stronger interaction forces. See e.g., Henck, 1997. *Tribology Letters* 3:239. Although this problem is present in larger scale DNA processing devices, it is considerably exacerbated in micro-machined devices with larger surface to volume ratios. It is also a problem in DNA processing systems such as PCR reactors, capillary and plate gel electrophoresis systems.

Surface interactions have been addressed for a microfabricated polymerase chain reaction ("PCR") device (see e.g., Shoffner, et al., 1996. *Nuc. Acids Res.* 24:375. Additionally, several types of surface treatments were investigated in an initial attempt to find PCR "friendly" surfaces, including surface treatment by silanization followed by a polymer treatment, by stoichiometric silicon nitride coating, and by silicon oxide coating. It should be noted, however, that only silicon oxide was demonstrated not to inhibit the PCR reaction; whereas the inhibition of the PCR amplification reaction by the other treatments methodologies was presumed to have been the result of surface binding sites that non-specifically adsorbed molecules involved in the PCR reaction (see e.g., Cheng, 1996. *Nuc. Acids Res.* 24:380.

Accordingly, it is apparent that there is a need for surface treatments for surfaces created in micro-machined DNA processing devices that inhibit DNA surface adsorption. Such an inhibition is termed herein surface "passivation."

It should be noted that citation of references herein is not to be taken as an admission that such references are prior art to the instant invention.

SUMMARY OF THE INVENTION

The present invention discloses the finding that certain surface treatments possess the ability to reduce DNA adsorption. For example, certain surface treatments are based upon: (i) plasma-enhanced, low temperature deposition of silicon oxide or (ii) low pressure chemical vapor deposition (hereinafter designated "LPCVD") of low temperature silicon oxide. In particular, the present invention discloses conditions (including precursors), deposition process conditions and subsequent process conditions, which provide for minimal adherence of DNA to a treated surface. Similarly, other surface treatments of the present invention are based upon LPCVD deposition of silicon nitride. In particular, the present invention discloses the finding that certain levels of silicon-enrichment possess novel and highly efficacious properties. Furthermore, the present invention discloses the finding that surface treatments, based upon low pH wash solutions, also markedly reduce DNA adsorption. These aforementioned treatments, as discloses herein, have been adapted to microfabrication processes which have, heretofore, only been utilized in the fabrication of miniaturized devices, primarily in the electronics industry.

Accordingly, one embodiment of the present invention discloses methodologies for the administration of these surface treatments to various types of DNA analysis devices. Another embodiment of the present invention discloses devices made by these methodologies which may be applied, for example, to the analysis of nucleic acids. In a preferred embodiment, the devices are improved DNA processing devices possessing surfaces to which have been administered the surface treatments and washes of the present invention. As these treatments reduce DNA adsorption, such improved devices may be advantageously further miniaturized with an attendant increase in the overall surface to volume ratios.

In a further embodiment, the present invention includes methods for assaying the extent of DNA adsorption to untreated and treated surfaces. These methods include, but are not limited to, washing the surfaces with fluorescently-labeled DNA, rinsing, and fluorescence detection of adsorbed DNA by use of a spectrofluorometry.

The instant invention also may be applied to both microfabricated and to larger scale DNA systems and devices. Such systems and devices may perform processing functions including, but not limited to: (i) DNA analysis (e.g., sequencing, separation, hybridization, electrophoresis; (ii) DNA processing (e.g., DNA replication, polymerase chain reaction ("PCR"), Reverse Transcription-basedPCR (RT-PCR), ligase chain reaction ("LCR"), in vitro transcription and translation, strand exchange with or without enzymes); (iii) DNA modifications (e.g., end- or internal-labeling, phosphorylation, de-phosphorylation,digestion, ligation, multiplex formation for strand identification); (iv) DNA packaging (e.g., linking to form higher ordered structures); and (v) DNA extraction.

In one embodiment, the present invention discloses a method for quantitatively ascertaining the level of adsorption of a nucleic acid to a surface comprising the steps: (i) contacting the treated surface with a solution of labeled nucleic acid molecules; (ii) washing this contacted surface so as to remove the labeled nucleic acid solution and (iii) measuring the amount of label still present on the treated surface. In a preferred embodiment, the nucleic acid is DNA and the label is fluorescent. The aforementioned treated surface is comprised of a nucleic acid processing device which contacts a medium containing nucleic acids, wherein the solution comprises said medium containing nucleic acid molecules in a concentration expected to be present in said device, and wherein the medium is allowed to contact the surface for a time representative of times that the medium contacts the surface during operation of the device.

In a second embodiment, the present invention discloses an apparatus for processing of nucleic acids which is comprised of one or more surfaces contacting a nucleic acid-containing medium and a surface film upon which is deposited a silicon-rich, silicon nitride deposit. Preferably, the silicone nitride surface film is deposited by a method comprising chemical vapor deposition. In one aspect of this embodiment, the silicon-rich, silicon nitride surface has the chemical composition, $SiN_x$, where that X is selected to minimize nucleic acid adsorption to the surface(s). In a preferred embodiment, X is a valve between approximately 0.8 and approximately 1.2, or, more preferably, is a valve between approximately 0.95 and approximately 1.05. In another aspect of this embodiment, the silicon-rich, silicon nitride possesses an index of refraction between approximately 2.1 and approximately 2.5, and more preferably between approximately 2.15 and approximately 2.25.

In a third embodiment, the present invention discloses an apparatus for the processing of nucleic acids comprising: one or more surfaces which contact a nucleic acid-containing medium and a surface film coating which is comprised of silicon oxide (possessing 1–4% by weight of hydroxyl groups and less than 0.5% by weight of hydride groups) deposited on the surface(s) by a chemical vapor deposition methodology.

In a fourth embodiment, the instant invention includes a method for producing an apparatus for processing nucleic acids comprising the step of depositing a coating of silicon oxide on one or more surfaces of said device that contact a medium containing nucleic acids, wherein the deposition is by chemical vapor deposition methodology performed at a temperature selected so as to minimize nucleic acid adsorption to the surface(s). This deposition temperature is preferably less than 500° C., more preferably less than 200° C., or most preferably less than 100° C.

In a fifth embodiment, the present invention discloses an apparatus for the processing of nucleic acids generated according to the methodology set forth in the fourth embodiment.

In a sixth embodiment, the present invention discloses a method for producing a device for processing nucleic acids comprising the step of washing the surface(s) of the device which contact a nucleic acid-containing medium with a specific washing solution. Preferably, the specific washing solution possesses a basic pH of at least 8, or is volatile, or is comprised of an oxidizing agent. In one aspect of the sixth embodiment, the specific washing solution comprises an alkalinizing agent selected from the group consisting of ammonium hydroxide ($NH_4OH$) and sodium hydroxide (NaOH). In another aspect of the sixth embodiment, the specific washing solution comprises an aqueous solution of ammonium hydroxide ($NH_4OH$) and the oxidizing agent hydrogen peroxide ($H_2O_2$), and preferably comprises a solution of approximately 4 parts of water, approximately 1 part of 30% $NH_4OH$, and approximately 1 part of 30% $H_2O_2$. Alternately, the concentration of the $NH_4OH$, the concentration of the $H_2O_2$, and the duration of the washing step are selected so as to minimize nucleic acid adsorption to the device's surfaces. In a preferred embodiment, the step of washing occurs at room temperature.

In a seventh embodiment, the present invention discloses an apparatus for processing nucleic acids generated according to the methodology of the sixth embodiment.

BRIEF DESCRIPTION OF THE DRAWINGS

These and other objects, features, and advantages of the invention will become apparent to those of skill in the art in view of the accompanying drawings, detailed description, and appended claims, where:

Figure 1A:
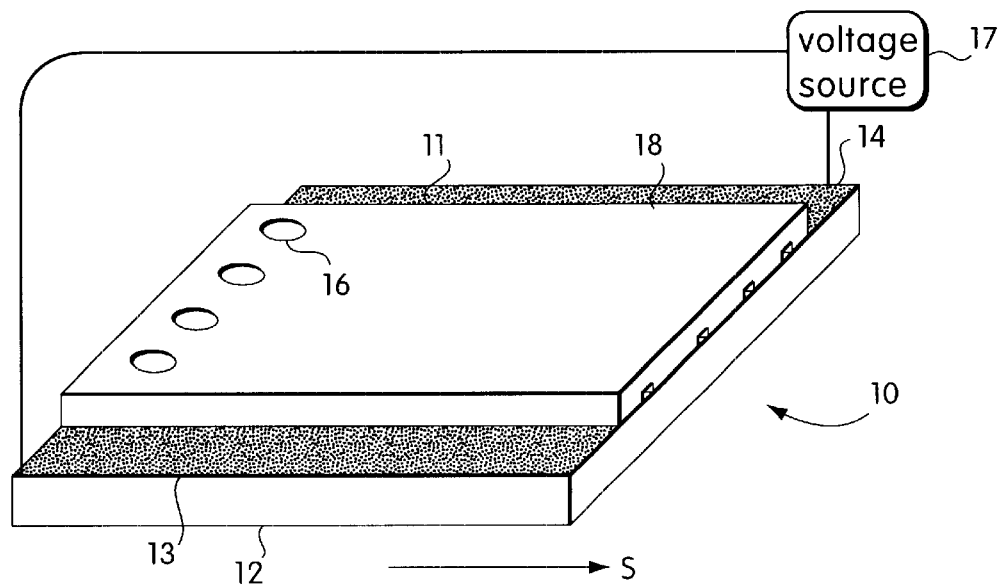
FIGS. 1A and 1B are drawings illustrating an exemplary embodiment of a microfabricated device for DNA processing to which the present invention is applicable.

Table 1 sets forth the measured DNA adsorption values of the various surface films of the invention after film deposition.

Table 2 sets forth the measured DNA adsorption values of the various surface films of the invention after surface washing.

Table 3 sets forth the surface interaction energies obtained from sessile drop contact angle measurements for the various surface films provided in Table 2 using the designated fluids.

DETAILED DESCRIPTION OF THE INVENTION

The present invention discloses methodologies providing surface treatments for processing devices of nucleic acids, as well as disclosing devices which possess such surface treatments. These treatments and devices are primarily directed to miniaturized devices having higher ratios of the surface areas which contact nucleic acid containing mediums to the volumes which contain such mediums. In such devices, it is particularly advantageous to reduce surface adsorption of the limited amount of contained nucleic acids.

It should be noted that the methods and devices discloses by the present invention are described with respect to their principal applications, which is to devices for processing DNA.

Accordingly, the treatments of the instant invention are designed to provide surfaces presenting little unwanted interaction with the DNA in mediums contacting the treated surface. These treatment include either deposition of a surface film, such as silicon rich silicon nitride, plasma enhanced chemical vapor deposited low temperature silicon oxide, or low pressure chemical vapor deposited ("LPCVD") silicon oxide on those surfaces exposed to DNA containing mediums, or by treating such surfaces with a high pH cleaning solution, such as solutions containing ammonium hydroxide and hydrogen peroxide, ammonium hydroxide alone, or sodium hydroxide alone.

These aforementioned treatments may be advantageously applied to DNA processing devices of all sizes and types. Although DNA adsorption is exacerbated in micromachined devices, it is also present in larger scale DNA processing devices. DNA apparatus include such well-known instruments as electrophoresis devices of all configurations, including gel slab, capillary, and micromachined. They further include processing devices such as reactors for performing PCR reactions, sequencing reactions, and other enzymatic reactions such restriction endonuclease digestion, ligation, and the like.

This section introduces the invention by disclosing, first, exemplary DNA processing devices, and second, exemplary surface treatment processes. In addition, the specific reaction conditions which are suitable for surface treatment are disclosed.

(i) Exemplary DNA Processing Devices

This subsection describes an exemplary DNA separation device and an exemplary DNA processing reactor configuration. Although two exemplary, miniaturized DNA processing devices are described in this subsection, it should be noted that this description in no way limits the present invention. One of ordinary skill within the art will readily appreciate how the methods of this invention can be applied to most types of DNA processing devices possessing surfaces which are amenable to the treatments disclosed herein.

Figure 1B:
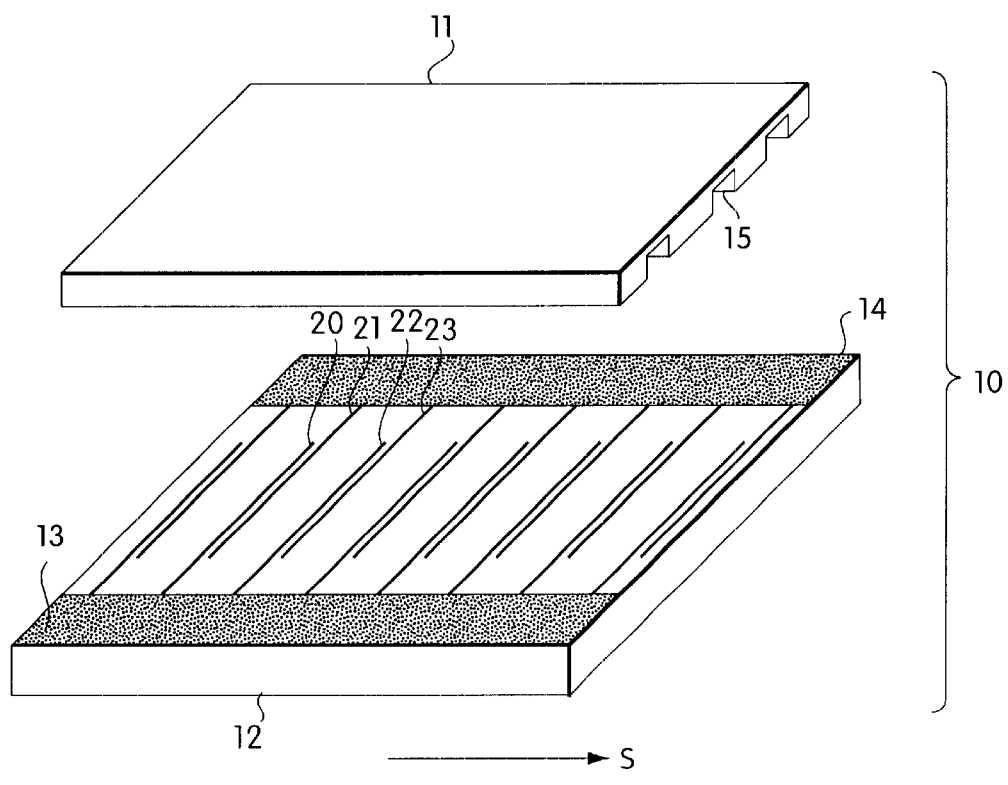

FIG. 1, Panels A and B illustrate a microfabricated device for the separation of nucleic acid fragments. Preferably, this device separates the nucleic acid fragment which are present in a liquid medium contained in channels in the device according to the differential diffusion inherent to each of the individual nucleic acid species present within the medium. The separation of each of the nucleic acid species is driven by a spatially and temporally varying electrical potential. The device utilizes an "on-state" and "off-state" during the separation procedure. In an "on-state", the electrical potential has a plurality of eccentrically-shaped potential wells which serve to trap charged particles (i.e., nucleic acids). In an "off-state", the electrical potential is flat, and the separation occurs as particles diffuse in a differential manner from well-to-well, based upon differences in diffusivity within the separation medium (see e.g., PCT Publication WO 97/36171).

As illustrated in FIG. 1, Panel B, the separation device of the present invention is configured with one or more physically-defined, separation lanes or channels (15) contained within the top cover (11) of the device which serves to confine the fluid medium and nucleic acid when the top cover is sealed to the substrate. As illustrated by FIG. 1, Panel A, the separation lanes (15) extend between the loading port (16) and observation zone (18). The substrate (11) may be comprised of glass or silicon or, alternately, materials such as quartz, sapphire or metals. As also illustrated by FIG. 1, Panel B, the spatially- and temporally-varying electrical potential is created by electrodes (20, 21, 22 and 23) connected to the bond pads (13 and 14) which are patterned on bottom plate (12). The electrodes are arranged in a transverse manner in relation to the direction of nucleic acid separation (S), and are positioned so as to create eccentric potential wells; wherein each well possesses a generally-eccentric, "sawtooth-like" shape when a voltage difference is applied by the external voltage source (17).

A separation device of the aforementioned configuration may be microfabricated. In such an apparatus, metallic electrode material is deposited on the bottom plate and etched into the desired configuration by standard microlithographic and etching methodologies which are applicable to the selected metal. Similarly, channels (which may be 25 μm or smaller) may be etched into the top cover (11) using similar processes applicable to the selected cover material. See e.g., PCT Publication WO 97/36171 for further a description of the microfabrication processes involved in the production of such an apparatus.

The nucleic acid-containing medium contacts several components of the apparatus, including the top cover (11) with channels (15), the bottom plate (12) and the plurality of electrodes (20, 21, 22 and 23). If the nucleic acid within the medium interacts and adheres with the surfaces of these aforementioned components, it may become adsorbed; in which case the nucleic acid detected at the observation zone (18) will be reduced or absent. Moreover, if these interactions are sufficiently strong, the nucleic acid may react chemically with surfaces, thus making the apparatus unusable for further separations. Such interactions have been observed in the case of silicon-based substrates. In order to insulate the electrodes from the silicon, a dielectric film is deposited or grown on the substrate prior to electrode formation. One example of a suitable film is silicon oxide which is grown by exposing the silicon substrate to elevated temperatures in an oxygen-containing atmosphere. However, it has been demonstrated that single-stranded DNA exhibited excessive adherence to such thermally-grown silicon oxide. Such adherence was markedly exacerbated by routine fabrication processes (e.g., the plasma process) which are utilized during the subsequent processing of the apparatus. Energetic interactions occurring within the plasma are capable of damaging the surface and increasing its reactivity. Because silicon processing is well understood, and silicon oxide is easily grown and widely utilized in microfabrication,a process to reduce the adherence of nucleic acids (i.e., single-stranded DNA) to thermally-grown silicon oxide will be highly advantageous.

Alternatively,an apparatus of similar configuration (but lacking the plurality of electrodes) may be used in the separation of nucleic acid fragments according to more conventional, gel-based electrophoretic methodologies. In such an apparatus, the separation channels (15) are filled with an appropriate gel matrix and an electrical potential is applied by electrodes arranged at each end of the separation channel. Similarly, in this apparatus, the nucleic acid-containing medium also comes in contact with several device components, and thus it is advantageous to reduce the overall level of nucleic acid adherence. A related, microfabricated electrophores is device is disclosed in PCT Publication WO 96/35810.

Figure 2:
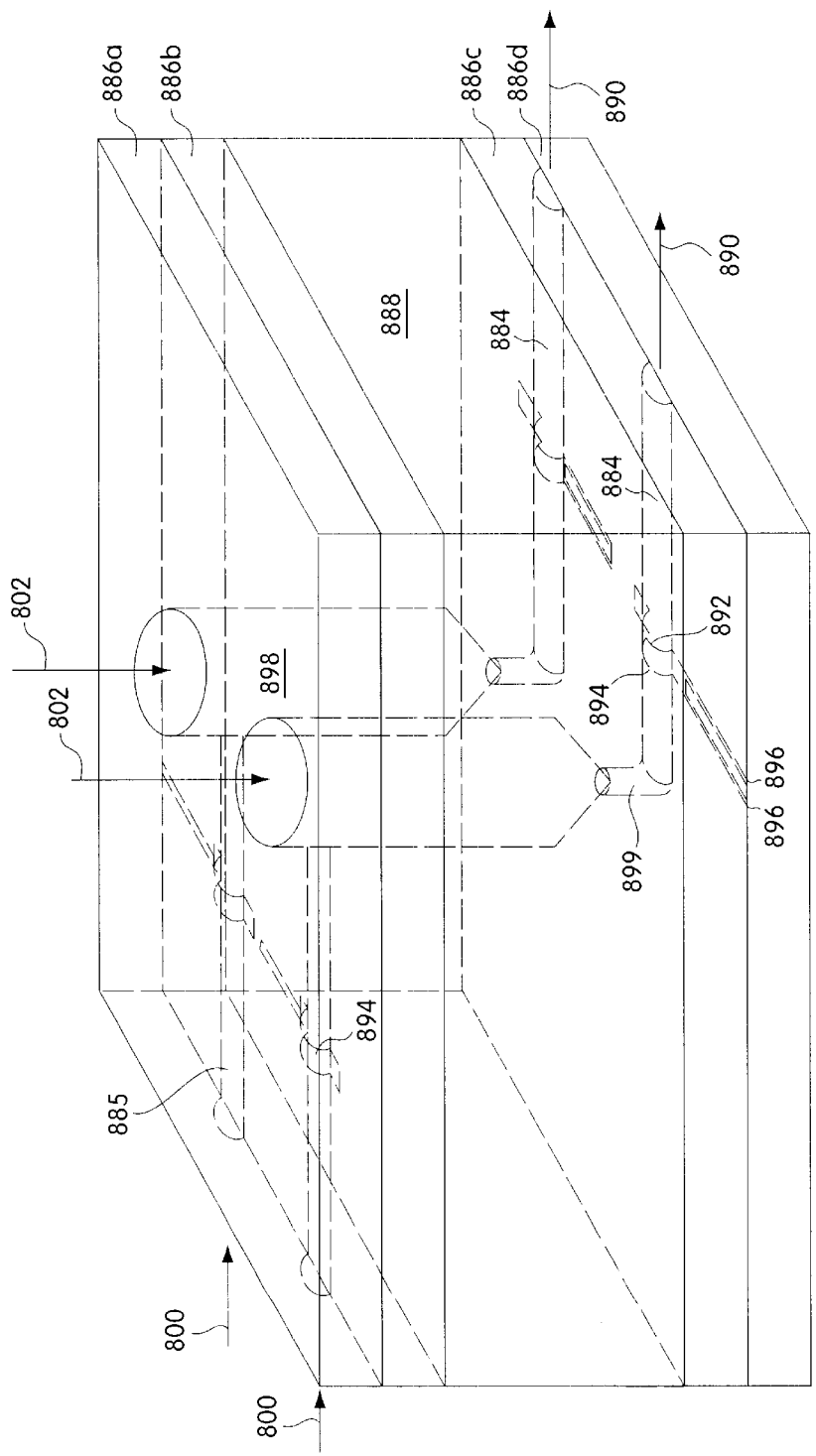
FIG. 2: illustrates another exemplary embodiment of a microfabricated device for DNA processing to which the present invention is applicable.

FIG. 2 illustrates a section of an exemplary nucleic acid processing reactor array. Illustrated are two micro-reactors (898), which are formed in substrate (888). These reactors hold reagents during the nucleic acid processing reactions (e.g., DNA sequencing reactions). The substrate (888) is typically comprised of glass, and the reactors (898) are typically microfabricated by either etching or drilling processes. The microreactors are supplied with reagents through both the top ports (802) and the inlet ports (800), which are conducted via inlet capillary channels (894 and 895) to the microreactors. Products are conducted to the outlet ports (890) by the outlet capillary channels (894) which are controlled by assemblies (894, 895 and 896), which may, preferably, be electrothermal microvalves. Inlet and outlet capillary channels are formed in substrates 866a and 866b and in substrates 866c and 866d, respectively. These substrates are typically silicon, and the capillaries are formed by micro-lithographic processes. The capillaries are then advantageously coated with a layer of, e.g., thermally grown silicon oxide to render them more inert. Design and fabrication of such a micro-reactor array are further described in, e.g., PCT publication WO 96/35810.

Also in such an apparatus, medium containing not only DNA, but also, for example, enzymes, reagents, labeled oligomers, and so forth, comes in contact with many device components. In particular, the capillaries have a higher surface to volume ratio and may be coated with thermally grown oxide. They are likely to undesirably capture molecules if they are reactive. Accordingly, it is also even more advantageous to reduce adherence, and especially DNA adherence, in such an apparatus.

Accordingly, surface treatments that generally obviate or eliminate DNA adherence to those surfaces advantageously used in microfabricated DNA processing devices of many types is useful and is achieved by the instant invention.

(ii) General Surface Treatments

Surface treatments which are useful for reducing nucleic acid adherence in microfabricated and larger nucleic acid processing devices generally include: (i) the deposition of certain films or coatings of controlled and desirable properties or (ii) the utilization of various surface washes designed to remove unwanted materials and leave the indigenous surface groups in a controlled state. The deposited films are applicable to a wider variety of surfaces including, but not limited to, silicon, silicon oxides, glasses, metals, plastics and other similar materials; where the surface washings are applicable, preferably, to surfaces comprised of silicon or silicon oxide. The following subsection will more-fully discuss both of these aforementioned types of surface treatments.

It should be noted that, although the following description is primarily directed to the reduction of DNA adsorption in DNA processing devices, the methodologies and devices discloses in the present invention are also adapted to the reduction of the adsorption of other nucleic acids (e.g., RNA, modified nucleic acids, nucleic acid mimics, and the like) in various devices which are designed for their processing. In addition, although these other aforementioned nucleic acids species possess somewhat different adsorption characteristics, the methodologies and devices disclosed herein may also be optimized, within the general ranges and compositions disclosed, for these different characteristics by means of the adsorption testing methodologies which will be discussed infra.

(a) Film Deposition

In a preferred embodiment of the present invention, deposited thin-films are formed of silicon nitrides or of silicon oxides and deposited by chemical vapor deposition (hereinafter "CVD") techniques. Preferred CVD techniques include low-pressure chemical vapor deposition ("LPCVD"), and plasma-enhanced chemical vapor deposition ("PECVD"). CVD-based deposition of films is widely-practiced in the fabrication of semiconductor integrated circuits. See e.g., Adams, 1988. "Dielectric and Polysilicon Film Deposition," In: *VLSI Technology*, $2^{nd}$ ed., pp. 233–271 (McGraw-Hill, Inc., New York, N.Y.), is hereby incorporated by reference in its entirety. The present invention is also adaptable to various other techniques for the depositing thin-films of these materials known within the art including, but not limited to: sputter or physical vapor deposition, evaporation, ion beam deposition and spin-on coating.

More specifically, CVD-based processes deposit films on substrates from gas phase reactants which are initially made highly reactive by various excitation means including, thermal heating, radio-frequency discharge, and the like. These processes may be performed in a variety of reactors and reactor configurations designed for the sequestering of substrates, with a variety of excitation means and under a variety of reaction process conditions. See e.g. Runyan & Bean, *Semiconductor Integrated Circuit Processing Technology* 1990. Pp. 121–160 (Addison-Wesley, Reading, Mass.), which is hereby incorporated by reference in its entirety.

Reactors and excitation means utilized in CVD-based deposition methodologies include, but are not limited to: (i) thermally-heated furnace tubes with an optional plasma glow discharge; (ii) continuous throughput, thermally-heated, atmospheric-pressure reactors and (iii) plasma-discharge reactors such as parallel-plate, inductively coupled plasma ("ICP"), and electron cyclotron resonance ("ECR") plasma-assisted CVD reactors. Thermally-heated furnace tubes are typically comprised of a quartz tube heated by a furnace into which the reactant gases injected at one end and evacuated (i. e., pumped) out of the other. The substrates utilized for deposition are typically held within a quartz holder, with the surface(s) which are to be coated spatially-oriented in an orthogonal manner to the incoming gas flow. Gas flow rates, temperature, and pressure are adjusted so as to control the film deposition rate, film uniformity, film structure, and other film properties. In a continuous-throughput, thermally-heated, atmospheric-pressure reactor, a conveyor assembly carries substrates through regions with thermally-heated reactant gases. These regions are bounded by gas curtains of fast-flowing jets of nitrogen. In plasma-discharge reactors, the reactant gases are excited by a high energy radio-frequency field which concomitantly creates a plasma discharge. Subsequently, reactant gas molecules flowing through the discharge are excited and ionized, thus forming a plasma and causing chemical reactions to occur. High intensity plasmas may be created by containing the radio-frequency-generated plasma by a magnetic field such as in the electron cyclotron resonance ("ECR") or by inductively-coupled plasma enhancement ("ICP") methodologies.

CVD-based process conditions for deposition of silicon oxides and nitrides include, but are not limited to, deposition temperatures which range from 100–1000° C., and operating pressures ranging from less than 1 milliTorr to atmospheric pressure (i. e., 760 Torr). Process times are adjusted according to desired film thickness, and may range from seconds to hours. CVD-based deposition process are preferred in the practice of the present invention due to the fact that they possess suitable film uniformity, film quality, and conformal step coverage.

The silicon nitride ("nitride") films of the present invention are not stoichiometric, but instead, are silicon-rich (i.e., possess silicon in excess of the amount in stoichiometric nitride). As utilized herein, stoichiometric nitride may be designated in either conventional chemical nomenclature as $Si_3N_4$ or, alternately, it may be designated as $SiN_x$, where for stoichiometric nitride X has a value of 1.33. Preferably, the silicon-rich nitride films of the present invention possess an X value which ranges from approximately 0.8 to approximately 1.2, and most preferably possess an X value which is substantially equal to 1 (i.e., approximately 0.95 to approximately 1.05). The excess silicon content of deposited nitride films may be advantageously monitored by measuring the index of refraction (i. e., the "refractive index") of the deposited film. For example, stoichiometric nitride films in which X has a value of 1.33, possess a refractive index of 2.01. Increased refractive indices, up to 2.5, are generally associated with the preferred silicon-rich heterogeneous film. See e.g., Adams, "Dielectric and Polysilicon Film Deposition," 1988. P. 261 In: *VLSI Technology*, $2^{nd}$ ed (McGraw-Hill, Inc., New York, N.Y.). With regards to refractive indices, the preferred silicon-rich nitride films of the present invention possess refractive indices which range from approximately 2.1 to approximately 2.5, and most preferably possess refractive indices which are substantially 2.2 (i. e., approximately 2.15 to approximately 2.25). The refractive index of a deposited nitride film may be conveniently measured by the methodology of ellipsometry. See e.g., Azzam, et al., 1989. *Ellipsometry and Polarized Light*, (North-Holland, New York); Tompkins, 1993. *A User's Guide to Ellipsometry*, (Academic Press, Boston, Mass.) which are hereby incorporated by reference in their entirety.

The preferred nitride films of the present invention may be deposited by the use of a number of CVD reaction chemistries, which may be selected depending upon limitations of available deposition equipment and the temperature constraints of the devices to be coated. For example, for plastic devices, process temperatures may not exceed the temperature which is destructive to the plastic materials. Chemically-deposited nitride is an amorphous dielectric. The amount of silicon which is incorporated within a nitride film is dependant upon various deposition parameters, and particularly, upon the ratio of Si and N reactants, as quantitatively determined from the vapor pressures of the gases providing these aforementioned reactants. In general, more silicon is incorporated at low nitrogen to silicon source ratios and at low deposition temperatures. Detailed process conditions are selected to achieve nitride films of the desired degree of silicon-richness, or equivalently, of the desired refractive index.

Suitable reaction chemistries include, but are not limited to: CVD, LPCVD and PECVD processes. In the CVD process methodology, nitride films may be formed by reacting silane ($SiH_4$) and ammonia ($NH_3$) at atmospheric pressure (i.e., 760 Torr) and at temperatures of 700–900° C. In the LPCVD process methodology, nitride films may be formed by reacting dichlorosilane ($SiH_2Cl_2$) and ammonia at temperatures of 700–850° C. and at reduced pressures of no more than 10 Torr. In the PECVD process methodology, nitride films may be formed by reacting silane with ammonia or nitrogen at temperatures of 200–400° C. and at intermediate pressures and with a plasma discharge.

More specifically, silicon oxide (hereinafter "oxide") films of the present invention preferably possess a integral "lattice" which contains adequate hydroxyl groups or ions (—OH or $OH^-$). A preferred range of hydroxyl group content ranges from approximately 1% by weight to approximately 4% by weight, as measured by various techniques known within the art (e.g., infrared (IR) spectroscopy). Generally, any fourrier transform-based IR spectroscopy instrument may be utilized, such as a Model 550 from Nicolet Instrument Corp (Madison, Wis.). It is also preferred that oxide films possess a minimum of hydride groups of hydride ions (—H or $H^-$). In a preferred embodiment of the present invention, oxide films posses less than approximately 1% by weight of hydride, and more preferably less than 0.5% or lower by weight of hydride, also as measured by IR spectroscopy.

Deposition process conditions are important in producing the preferred oxide films of the present invention. Importantly, oxide films deposited at the lowest practical temperatures generally contain the most hydroxyls and are the most preferred in the practice of the present invention. Such films may also be deposited according to a number of reaction chemistries. For example, in a preferred embodiment, silane and oxygen are allowed to react with a furnace tube preferably at temperatures lower than 500° C., or more preferably at temperatures lower than 200° C., or most preferably at temperatures lower than 100° C. and at pressures ranging from atmospheric to milliTorr. The most preferable temperatures of the present invention, range from room temperature to a maximum of approximately 120–150° C. It should be noted that, tetraethoxysilane(Si $(OEt)_4$) or other organosilanescan be decomposed at higher temperatures, 650 to 750° C. in an LPCVD or PECVD reactor with pressures ranging from sub milliTorr to tens of Torr. Much less preferably, at even higher temperatures near 900° C., reactions of dichlorosilane and nitrous oxide can yield oxide films. However, these latter films do not contain sufficient hydroxyl to be advantageous for this invention.

Films of both materials have a preferred thickness between 2–2000 nm (or more), with films of order 100 nm in thickness the most preferred embodiment, in order to prevent adverse DNA adsorption. The minimum thickness is determined as that film thickness that effectively separates the original device surface from a DNA containing medium, and prevents properties of the original surface from having an interaction with the DNA in the medium beyond the deposited film. The maximum thickness can be any thickness that is structurally achievable and suitable for the processing device to be treated. Typically, the film thickness is determined by the duration of the deposition. The relative between the deposited film thickness and the deposition time is be dependent on the exact reactor and process parameters used.

Figure 5:
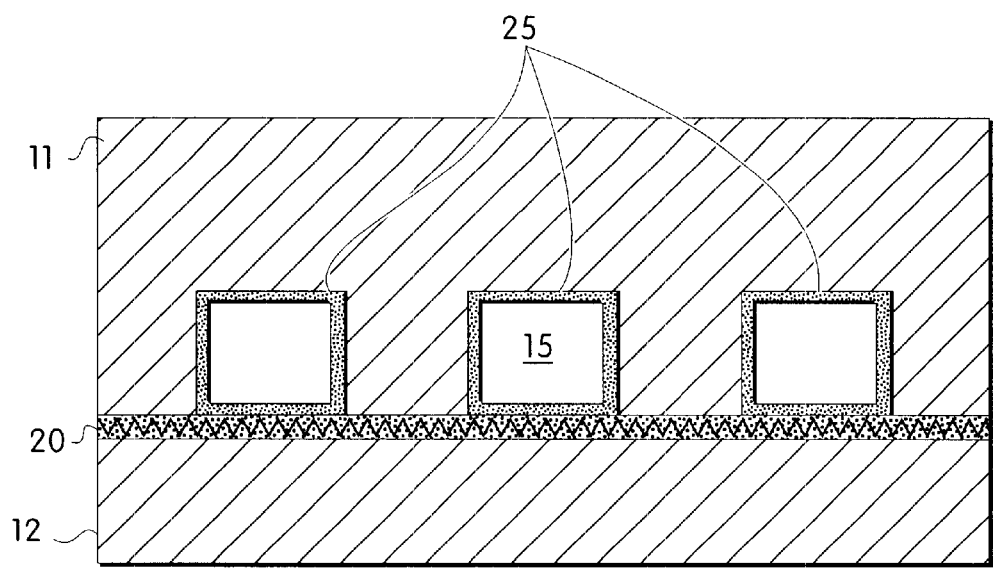
FIG. 5: illustrates a cross sectional view of the exemplary device of FIG. 1 following surface coating as disclosed in the present invention.

FIG. 5 illustrates an exemplary application of the deposited films of the instant invention to the DNA separation device of FIG. 1, Panels A–B. FIG. 5 illustrates channels (15) bounded by substrate (11) and bottom plate (12) and having electrodes (20) deposited on its surface. Film (25) has been deposited, as previously described, on the channel boundaries in substrate (11) and on those portions of electrodes (20) and the remainder of bottom plate (12) which are exposed to the DNA containing medium. Accordingly, since the DNA containing medium contacts only deposited film (25), unwanted DNA adsorption is reduced.

(b) Surface Washes

With regard to surface washings, it has been demonstrated that certain basic surface washings advantageously reduce DNA adherence. Such basic surface washings are believed to function by leaving reactive sites on a surface terminated by neutral, hydrophilic hydroxyl groups. DNA has reduced affinity to such neutral, hydrophilic, basic surfaces. Suitable basic wash solutions contain an alkalinizing agent in a solvation fluid which cause the pH or the solution to be 8, 10, 12, 14, or higher. Suitable solvation fluids includes water, and alcohols (e.g., methanol (MeOH) or ethanol (EtOH)) and, in particular an EtOH/KOH solution, are adaptable to the present invention. Suitable alkalinizing agents include ammonium hydroxide ($NH_4OH$), potassium hydroxide (KOH), sodium hydroxide (NaOH), or other bases. An optional, but preferred embodiment includes oxidizing agents in order to oxidize (and thereby remove) residual organic contaminants left from any previous microfabrication steps. Suitable oxidizing agents include peroxides, chlorates, perchlorates, nitrates, permanganates, and so forth. Most preferred solvation, alkalinizing, and oxidizing agents are easily volatile without leaving any residues.

Preferred surface washing solutions include aqueous (solvation agent) solutions of ammonium hydroxide or sodium hydroxide (alkalinizing agents) in combination with hydrogen peroxide ($H_2O_2$) (oxidizing agent). A most preferred surface washing solution includes approximately 4 parts water, approximately 1 part 30% hydrogen peroxide, and approximately 1 part 30% ammonium hydroxide. This latter solution is most preferred because, first, all its components are volatile and leave no residue on a surface, and because, second, it is strongly oxidizing and is capable of oxidizing and removing organic surface contaminants. A broad range of compositions are most preferred, as long as sufficient ammonium hydroxide is present so that the wash solution is sufficiently basic and sufficient hydrogen peroxide is present so that expected organic surface contaminants can be oxidized. The reagents are preferably of such a purity (i.e., reagent grade) such that they leave no contaminants themselves upon volatilizing from a surface.

Device surfaces to be treated are exposed to the wash solution at room temperature for a time period preferably from 1 minute to 1 hour with a 10 minute wash being the most preferred embodiment. The present invention is also adaptable to shorter or longer exposures, as well as to exposures at elevated temperatures, up to the actual boiling point of the wash solution. Following this treatment, the surfaces are then rinsed with water, preferably deionized water, so as to remove any remaining wash solution. The equipment utilized for exposing surfaces is typically either an immersion bath (with or without ultrasonic agitation) or a spin-spray device.

Semiconductor processing also uses surface washings and chemical cleanings, although typically with markedly different processing parameters than disclosed herein in the preferred embodiment. See e.g., Runyan, et al, 1990. *Semiconductor Integrated Circuit Processing Technology* pp. 99–104 (Addison-Wesley;Reading, Mass.). Surface exposure to wash solutions is typically at a temperature ranging from 75° C. to near 100° C. Sodium hydroxide solutions are not typically utilized in semiconductor processing, due to the potential contaminating effect of this alkali metal (i. e., sodium) including reduction of integrated circuit oxide field and charge build up in the oxide insulator. Hydrogen peroxide with ammonium hydroxide or hydrochloric acid has also been used as part of a cleaning routine referred to as the "RCA Clean" (see e.g., Kern & Puotinen, 1970. *RCA Review* 31: 187, which is hereby incorporated by reference in its entirety). However, in semiconductor processing, a final acidic wash is generally always performed in order to remove contaminating metallic species. Such a final acidic wash would destroy the hydroxylated surface which the present invention is dependent upon, thus resulting in the formation of a charged surface capable of interacting with DNA.

(iii) Evaluation of Surface Treatments

Surface treatment methodologies may be evaluated according to several metrics (see e.g., Ulman, 1991. *An Introduction to Ultrathin Organic Films* pp. 1–100 (Academic Press; San Diego, Calif.), which book is hereby incorporated by reference in its entirety). The subsequent subsection discloses, first, a methodology for directly testing DNA adsorption and second, a methodology for evaluating surface interaction energy.

Advantageously, DNA adhesion to surfaces in a DNA processing device may be directly tested by: (i) contacting the surfaces of interest with a DNA containing medium which is likely to be present in the device; (ii) washing DNA not adsorbed to the surface under conditions expected in the device and (iii) measuring the remaining adsorbed DNA. Measurements of adsorbed DNA may be performed according to any method known within the art, in particular by measuring fluorescent emission of a fluorescent label which may be conjugated to DNA. Any convenient fluorescent label known within the art for nucleic acid labeling may be used. Various surface treatments (as well as the lack of surface treatment) may be evaluated by comparing the DNA adsorptions by, for example, comparing fluorescent emissions from the surfaces.

More specifically, a preferred embodiment for the aforementioned measurement in the case of a DNA separation device proceeds according to the following steps. It should be noted, however, that for other types of devices, the conditions would be suitably varied to those expected or required for the other devices. A representatively-dilute solution of fluorescently-labeled DNA fragments is placed upon the surface of interest for a period of time representative of the duration of contact which is generally expected during actual operation of the given device (typically several minutes). Subsequently, the surface is rinsed in deionized water for approximately 30 seconds. Following the rinse, the surface is dried, and any florescent (and hence fluorescently-labeled DNA) emissions measured.

Figure 3:
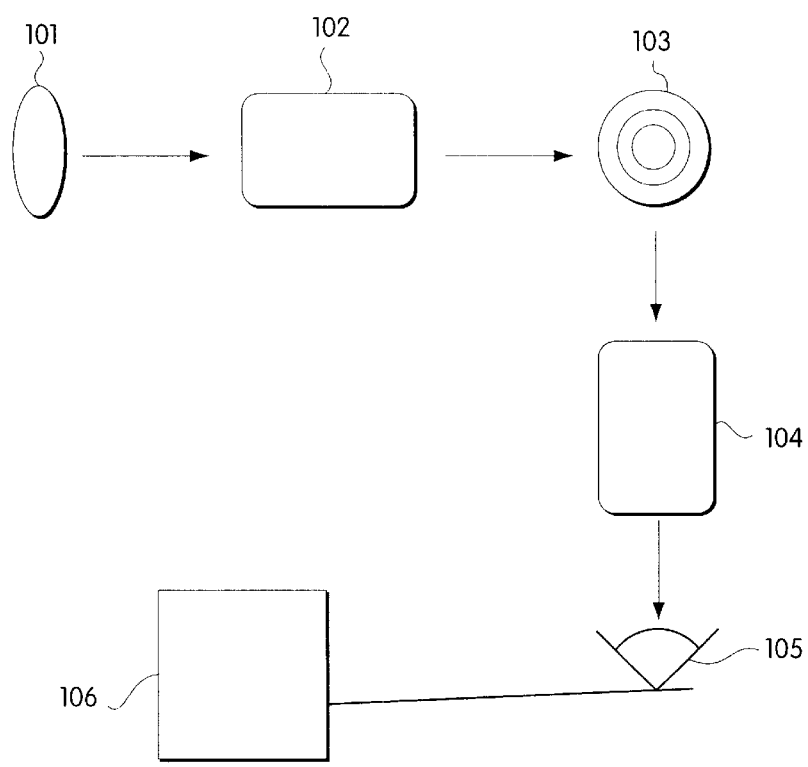
FIG. 3: illustrates a block diagram of a spectrofluorometerused as disclosed by the present invention.
Figure 4A:
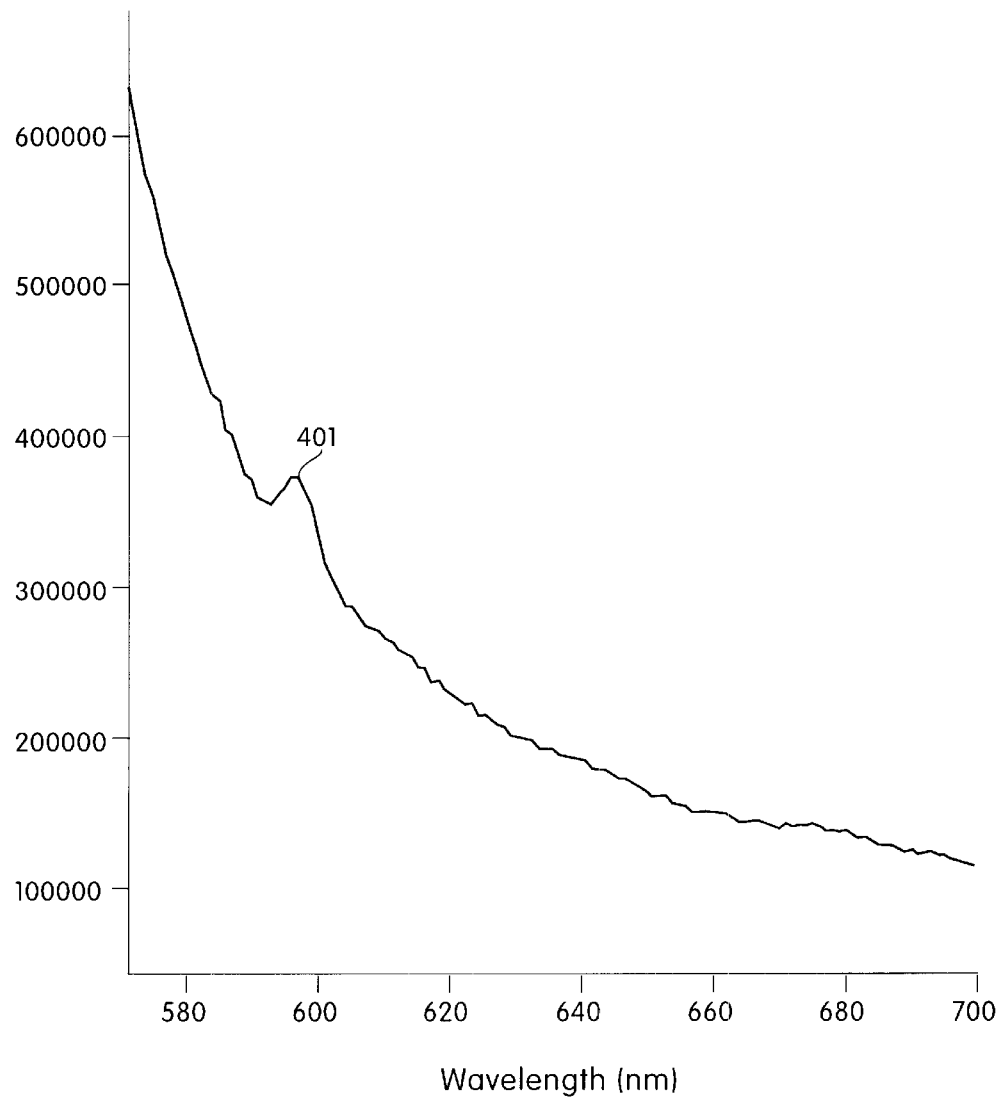
FIG. 4A is a graph illustrating the fluorescent emission spectra near 600 nm used to detect and measure the level of ROX-labeled DNA adsorbed to various treated surfaces of the invention, The graph illustrates a peak fluorescence (401) from stoichiometric LPCVD silicon nitride washed with a ROX DNA solution.
Figure 4B:
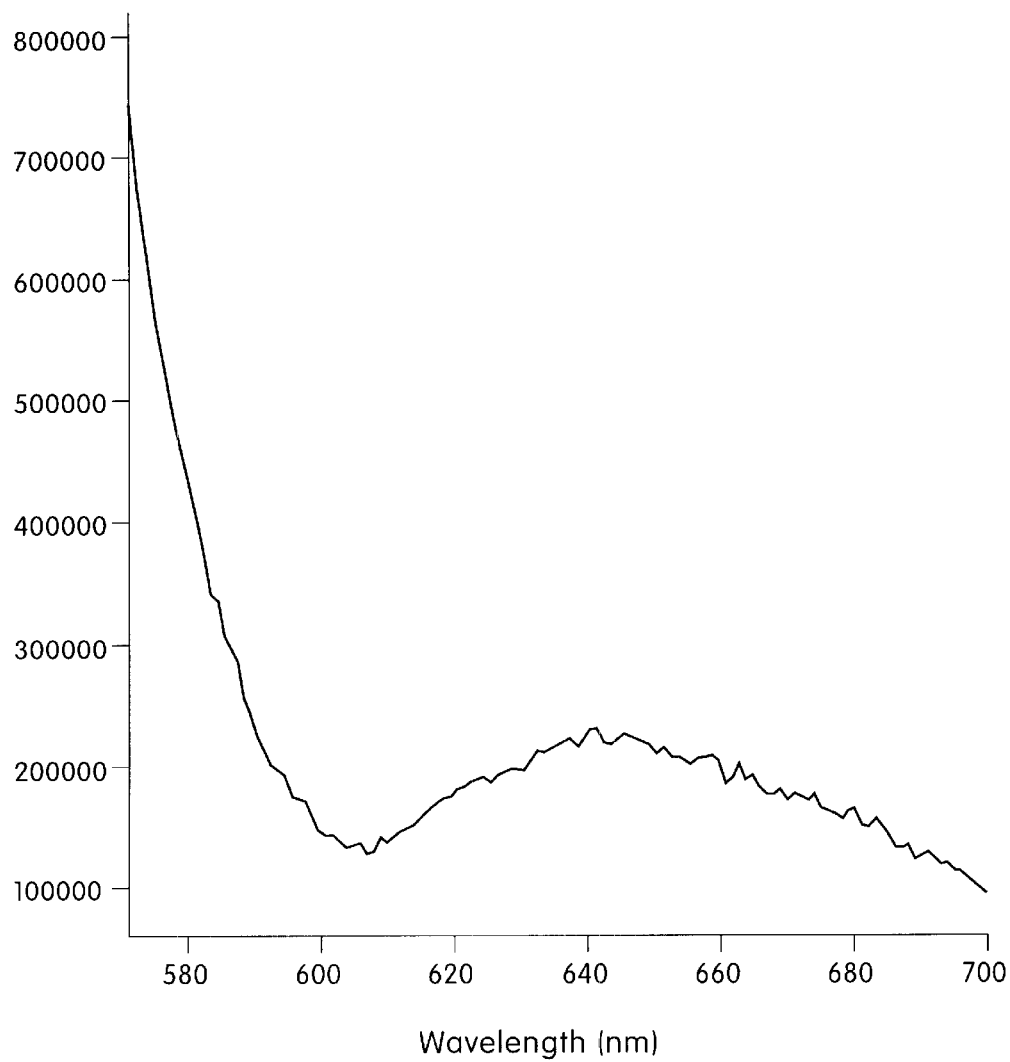
FIG. 4B is a graph illustrating the lack of fluorescence near 600 nm observed from a LPCVD silicon rich silicon nitride surface washed with a ROX-labeled DNA solution.
Figure 4C:
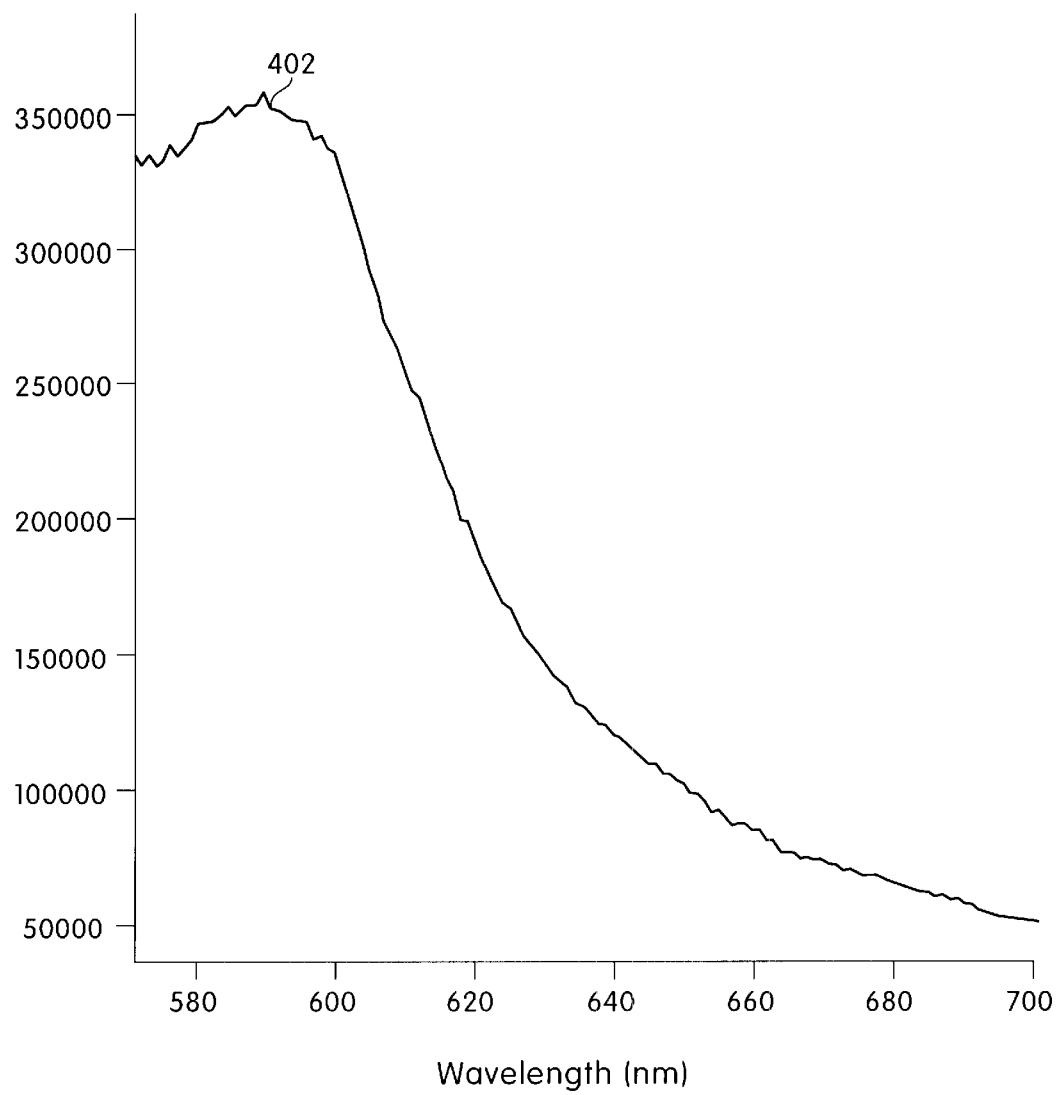
FIG. 4C is a graph illustrating a peak fluorescence (402) from the surface of thermally grown silicon oxide treated by the standard device fabrication methodology (i. e., coated with a photoresist and ashed) and washed with a ROX-labeled DNA solution.
Figure 4D:
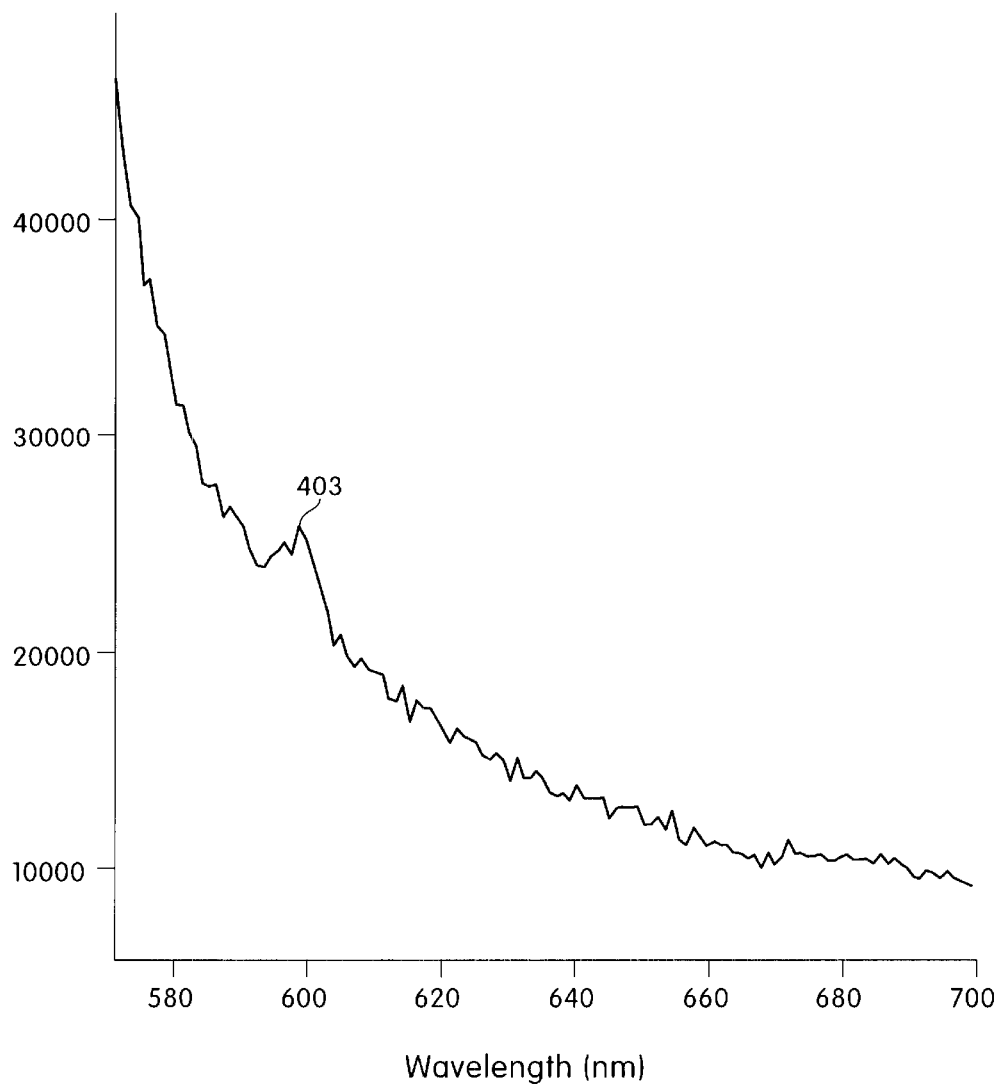
FIG. 4D is a graph illustrating a greatly reduced peak fluorescence (403), when compared to the graph shown in FIG. 4C, from the surface of a thermally grown silicon oxide surface treated as in FIG. 4C, washed with an ammonium hydroxide/hydrogen peroxide solution described herein, and subsequently washed with a ROX-labeled DNA solution.

Fluorescent emissions from adsorbed DNA, if any, may be measured by obliquely illuminating the surface with a light source so as to stimulate emissions, and observing emissions in a substantially-perpendicular orientation to the surface. This spatial orientation is utilized so as to eliminate interference from light scattered from the stimulating source. Measurements may be made of either the spectrum in the vicinity of the emission maxima of the fluorescent label or, simply, of the total intensity near the maxima. These spectral measurements may be advantageously performed by placing the substrate at an oblique angle in a spectrofluorometer, such as a FluoroMax-2 (Instruments S.A., Inc.; Edison, N.J.). FIG. 3 illustrates a block diagram of such a measurement arrangement and process. Typically, light from xenon lamp (101) enters excitation spectrometer (102), which sends substantially monochromatic light of the appropriate selected wavelength to sample (103). Light emitted from the sample is dispersed by emission spectrometer (104), and directed to photomultiplier detector (105). Emission spectra and total intensities may be recorded under control of computer (106) by scanning the emission spectrometer.

An exemplary fluorescent dye of the present invention is carboxy-X-rhodamine ("ROX"), which has a stimulation maximum near 550 nm and an emission maxima near 600 nm. A 550 nm light source may be utilized for excitation of ROX, and the resulting emission spectra from 575 nm to 700 nm may be recorded. FIG. 4, Panels A–D, illustrate sample emission spectra measured from surfaces tested for DNA adherence according to the aforementioned protocol.

Advantageously, the methodology for the testing of DNA adhesion as disclosed herein may also be applied to the determination of the optimum parameters for the various deposited films and surface washing of the present invention. The previous description gives general guidance for selecting preferable parameters for the silicon-rich nitride films, the low temperature, hydroxyl-containing oxide films, and the basic and, optionally, oxidizing washes of the present invention. However, in each application, obtaining optimum films may require some variation of the preferred parameters, at least for the following reasons. In the case of surface washes, each surface to be treated possesses particular characteristics which may require process individualization. In the case of deposited films, CVD reaction equipment has particular characteristics which may require adjustment to deposition parameters. Such parameter variation and adjustment may be systematically performed according to the present invention by a methodology of: (i) performing a plurality of surface treatments according to controlled changes in the relevant treatment parameters; (ii) measuring DNA adsorption to the treated surfaces according to the described testing method and (iii) selecting those process combinations giving suitable or optimum results. In the case where several parameters need to be varied, the previous methodology may advantageously be repeated in order to efficiently search the multi-dimensional parameter value space for suitable or optimum joint values of the several parameters. Generally, the most preferred films of this invention are those produced by the methods of this invention whose process parameters have been optimized by a method, such as that described supra.

Measurements of the interaction energy between surfaces and various fluids are typically utilized to evaluate surfaces. See e.g., Ulman, 1991. *An Introduction to Ultrathin Organic Films* pp. 48–58 (Academic Press; San Diego, Calif.). In particular, adhesion or adsorption of molecules to a surface has been observed energy to relate to surface interaction energy. See e.g., De Gennes, 1985. *Rev. Mod. Phys.* 57:827, which is hereby incorporated by reference in its entirety. Due to the fact that surface wetting of a fluid is also dependent upon interaction energy, an individual of average skill within the relevant art would expect that the more a fluid wets a surface, the more likely molecules soluble in that fluid would adhere or adsorb to that surface. Accordingly, a surface treatments which decreased wetting to reduce adsorption of, for example, DNA molecules, would be selected.

Simple wetting measurements provide an advantageous manner for the measurement of such interaction energy and for accessing the expectation for surface adhesion. One such measurement methodology observes sessile drop contact angles. In this technique, the overall shape of a liquid drop (which is the result of the free energy of the drop) upon a homogeneous, planar solid-surface is used to estimate the free energy of the surface. See e.g, Ulman, 1991. *An Introduction to Utrath in Organic Films* p. 481. (Academic Press; San Diego, Calif.). Generally, if there is no interaction between a surface and the liquid, the contact angle will be high, approaching 180°, and the overall shape of the drop will be more spherical. Conversely, as the interaction increases, the liquid spreads until the contact angle approaches 0°, and the drop will be more flattened in shape.

(iv) SPECIFIC EXAMPLE

The present invention is further described in the following specific examples, which are in no way intended to limit the scope of the invention disclosed herein.

Example 1

Film Deposition

A preferred LPCVD silicon rich nitride film, 960 nm thick, was deposited on a silicon <100> wafer in a Tylan furnace tube (Tylan General Inc.; San Diego, Calif.) at 835° C. using a dichlorosilane flow of 100 sccm (standard cubic centimeters per minute) and an ammonia flow of 25 sccm with a chamber pressure of 150 milliTorr. As evidenced by the relatively high index of refraction (i. e., N=2.2), this film is not stoichiometric, and is most probably approximately SiN stoichiometric rather than $Si_3N_4$ (see e.g., Adams, "Dielectric and Polysilicon Film Deposition," 1988. in: *VLSI Technology*, $2^{nd}$ ed, (McGraw-Hill, Inc.; New York, N.Y.).

The plasma-enhanced, CVD low temperature oxide ("PECVD LTO") was an ECR plasma-assisted (Plasma Quest Inc., Richardson, Tex.) deposited oxide. It was deposited at a substrate temperature less than 120° C. using gas flow rates of 100 sccm of silane, 20 sccm of oxygen, 120 sccm of argon, a chamber pressure to 6 milliTorr and a power of 350 W at 2 GHz, with 185 amps applied to the upper magnet, and was 290 nm thick. It should be noted that this deposited film is preferred for those surfaces which are damaged by higher temperatures (e.g., plastic surfaces). The LPCVD low temperature oxide ("LPCVD LTO") was deposited in a Tylan furnace tube (Tylan General Inc.; San Diego, Calif.) at 450° C. using flow rates of 60 sccm for silane and 90 sccm for oxygen and a chamber pressure of 300 milliTorr, and was 250 nm thick. Because the deposition temperature of these reactions was low, one of average skill within the art will generally recognize that the stoichiometry and, especially, the surface structure of these films will be heterogeneous (see e.g., Adams, "Dielectric and Polysilicon Film Deposition," 1988. in: *VLSI Technology*, $2^{nd}$ ed., pp. 259–260 (McGraw-Hill, Inc.; New York, N.Y.).

Table 1 sets forth the measured DNA adsorption values of the preferred surface films of the present invention, deposited as described above, as well as the measured DNA adsorption of certain other, less preferred, surface films. The other surface films which are utilized for comparative purposes include: (i) a 100 nm thick thermally-grown oxide (Tylan furnace tube; 1000° C. for 10 minutes); (ii) a 380 nm thick poly-hexane film (rf-deposited mixture of hexanes and methycyclopentane; 150 watts, 150 milliTorr pressure); (iii) Teflon AF (DuPont AF 1601; amorphous fluoropolymer spun on at 5000 RPM and cured on hot plates for 5 minutes at 90° C., 5 minutes at 170° C. and 5 minutes at 325° C.); (iv) a 450 nm thick spin-on-glass film (Allied Signal Accuglass 512, methylsiloxane polymer, spun on at 3000 RPM and baked on hot plates for 5 minutes at 90° C., 5 minutes at 170° C., 5 minutes at 275° C., and cured in a Tylan tube furnace for 30 minutes at 425° C. in nitrogen); (v) a 140 nm thick LPCVD stoichiometric nitride (Tylan furnace at 835° C., 25 sccm dichlorosilane, 200 sccm ammonia at 300 milliTorr) and (vi) a 1200 nm thick photoresist film (OCG 825 g-line resist spun on at 5000 RPM and soft-baked for 1 minute at 90° C.).

DNA adsorption to these aforementioned treated surfaces were measured as previously described herein. In all the cases, the DNA adsorption testing protocol was used with a $4 \times 10^6$ M (4 pM/µl) solution of DNA oligonucleotides with a length of 10 nt. which were labeled with carboxy-X-rhodamine("ROX"). Both the emission intensity near 600 nm (i.e., the emission maxima of ROX) and the spectra from 575 to 700 nm were measured as previously described. As illustrated in FIG. 4, Panels A–D, which set forth various surface emission spectra, the vertical axes of the graphs indicate the photo emission counts per second, and the horizontal axes indicate the wavelength of the emission.

Table 1 lists the observed emission intensity near 600 nm. As the results illustrate, silicon rich silicon nitride films and the two deposited oxide films retain significantly less DNA than simple thermal oxide film, or the other dielectric films. In fact, for the nitride and the PECVD LTO films no discernible emission peak above the excitation background was observed. This demonstrates that these coating greatly reduced or eliminated DNA adsorption.

This result is unexpected since, for among other reasons, those films are likely to be non-stoichiometric, and thus possess a less well-defined surface chemistry with more "dangling" bonds which tend to enhance DNA surface adsorption. However, by comparing the spectra shown in FIG. 4, Panel A and FIG. 4, Panel B, the reduced or eliminated emission near 600 nm from the ROX label of the DNA adhering to the surfaces which differ primarily in their stoichiometry, is illustrated. In particular, emission peak 401 (near 600 nm) in FIG. 4, Panel A is absent from FIG. 4, Panel B.

Example 2

Surface Washing

The surface washing methodology as disclosed in the present invention reduces DNA adsorption of thermally-oxidized silicon surfaces and is also applicable to the treatemt of various other surfaces as well. Initially, six silicon <100> surface were thermally-oxidized in a Tylan furnace at 1000° C. for 10 minutes so as to create an oxide layer approximately 100 nm thick. Residual fluorescence emission, following washing with fluorescently-labeled DNA, was subsequently measured as described supra. Table 2 sets forth the emission intensity near 600 nm from these surface after the previously described DNA adsorption testing protocol.

Surface 1 is a as-grown thermal oxide surface. Surface 2 is the thermal oxide surface following the preferred surface washing. Surfaces 3–6 have been coated with hexamethyldisilazane, ("HMDS"), and a photoresist. This is representative of the subsequent processing which occurs during the microfabrication of typical DNA processing devices. The photoresist on Surfaces 3 and 4 was removed using a standard photoresist ash process in a radio frequency oxygen plasma. The photoresist on Surfaces 5 and 6 was removed using a liquid photoresist stripper, PR-2000 (J.T. Baker Inc.; Phillipsburg, N.J.), which is an organic solvent-based solution used to dissolve the photoresist from surfaces.

The preferred washing of the present invention involved treating Surfaces 1–6 of Table 2 with an aqueous mixture of water, ammonium hydroxide (30%), and hydrogen peroxide (30%) at a ration of 4:1:1 (v/v/v) at room temperature for a total of 10 minutes in an immersion bath. Following treatment, the wafer was then rinsed with deionized water to facilitate the removal of any residual wash solution. As a result of the aforementioned washing step, a dramatic reduction in the residual fluorescence was demonstrated.

This reduction in measured residual surface fluorescence is further illustrated by comparing the spectra shown in FIG. 4, Panel C from Surface 3 and FIG. 4, Panel D from Surface 4. As illustrated, the overall reduction in adhered DNA due to ammonium hydroxide/hydrogenperoxide treatment is evident from the greatly reduced emission near 600 nm from the ROX label of adsorbed DNA. In particular, larger emission peak 402 in FIG. 4, Panel C is reduced to smaller emission peak 403 in FIG. 4, Panel D (with both peaks being near 600 nm). These results demonstrate the effectiveness of the basic and oxidative washes in greatly reducing DNA adsorption to a wide variety of surfaces.

Example 3

Surface Energy

The results of the aforementioned surface treatments set forth in Specific Examples 1 and 2 supra, are rather unexpected, due to the fact that they are not explained on the basis of surface energy. Table 3 below illustrates the results obtained from a series of sessile drop contact angle measurements for water, diiodomethane and hexadecane for Surfaces 1–6 of Table 2, supra. As previously discussed, DNA adsorption is generally expected to increase as surface interaction energies increase. Moreover, surface interaction energies are also reflected by "wetability" properties such drop contact angles.

There is clearly no correlation between the observed behavior of the DNA and the surface energy as measured by contact angles. For example, LPCVD silicon-rich silicon nitride and LPCVD stoichiometric silicon nitride possess substantially the same wetting properties (and thus surface interaction energies), but have dramatically different DNA adherence properties. Furthermore, Teflon AF, Spin-on-Glass and Poly-Hexane (which possess the highest contact angle, and thus the lowest surface energies) also tend to exhibit among the highest and most undesirable DNA adhesion levels. Finally, although both the PECVD and LPCVD LTO oxide film treatments and the native, thermally-grown oxide of Surface 1 possess substantially the same wetability properties, the preferred oxide treatments of the present invention result in between ½ and ⅓ less DNA adsorption than the simple, thermally-grown oxide.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for reducing the amount of nucleic acid bound to one or more surfaces used in a device for contacting a medium containing nucleic acids, the method comprising:
    washing the one or more surfaces with an alkaline solution comprising an oxidizing agent, wherein said solution is at a temperature between room temperature and 75° C.

2. The method of claim 1, wherein said alkaline solution has a pH of at least 8.0.

3. The method of claim 1, wherein said alkaline solution is volatile.

4. The method of claim 1, wherein said alkaline solution comprises an alkalinizing agent selected from the group consisting of ammonium hydroxide ($NH_4OH$) and sodium hydroxide (NaOH).

5. The method of claim 1, wherein said alkaline solution comprises an oxidizing agent.

6. The method of claim 1, wherein said alkaline solution comprises an aqueous solution of ammonium hydroxide ($NH_4OH$) and hydrogen peroxide ($H_2O_2$).

7. The method of claim 6, wherein the concentration of said ammonium hydroxide ($NH_4OH$), the concentration of said hydrogen peroxide ($H_2O_2$) and the duration of said washing are selected so as to minimize nucleic acid adsorption to said one or more surfaces.

8. The method of claim 1, wherein said alkaline solution comprises a solution of approximately 4 parts of water, approximately 1 part of 30% ammonium hydroxide ($NH_4OH$) and approximately 1 part of 30% hydrogen peroxide ($H_2O_2$).

9. The method of claim 1, wherein said washing occurs at room temperature.

10. The method of claim 1, wherein said solution has a pH of at least 10.

11. The method of claim 1, wherein said solution has a pH of at least 12.

12. The method of claim 1, wherein at least one of said surfaces is a silicon surface.

13. The method of claim 12, wherein said silicon surface is coated with hexamethyldisilizane (HMDS) or a photoresist.

14. The method of claim 1, wherein said solution is in contact with said surfaces for one minute to one hour.

15. The method of claim 1, wherein said solution is in contact with said surfaces for ten minutes.

16. The method of claim 1, wherein said solution comprises an alcohol.

17. The method of claim 16, wherein said alcohol is methanol or ethanol.

18. The method of claim 1, wherein said alkaline solution comprises a potassium hydroxide (KOH) alkalinizing agent.

19. The method of claim 18, wherein said alkaline solution comprises ethanol and potassium hydroxide.

20. The method described in claim 1 wherein the temperature is room temperature.

21. A method for minimizing adsorption of nucleic acids to a surface, the method comprising:
    providing a device comprising a surface for contacting a medium containing nucleic acids thereby minimizing adsorption of nucleic acids to a surface; and
    treating said surface with an alkaline solution comprising an oxidizing agent, wherein said solution is at a temperature between room temperature and 75° C.

22. The method of claim 21, wherein said surface is a silicon surface.

23. The method of claim 21, wherein said alkaline solution comprises an alkalinizing agent selected from the group consisting of ammonium hydroxide ($NH_4OH$) and sodium hydroxide (NaOH).

24. The method of claim 21, wherein said alkaline solution comprises an oxidizing agent.

25. The method of claim 21, wherein said alkaline solution comprises an aqueous solution of ammonium hydroxide ($NH_4OH$) and hydrogen peroxide ($H_2O_2$).

26. The method of claim 21, wherein said alkaline solution comprises a solution of approximately 4 parts of water, approximately 1 part of 30% ammonium hydroxide ($NH_4OH$) and approximately 1 part of 30% hydrogen peroxide ($H_2O_2$).

27. The method of claim 21, wherein said solution has a pH of at least 10.

28. The method described in claim 21 wherein the temperature is room temperature.

29. A method for minimizing adsorption of a nucleic acid to a surface, the method comprising treating said surface with a fluid comprising an alkalinizing agent and an oxidizing agent under conditions sufficient to minimize adsorption of a nucleic acid to said surface.

30. The method of claim 29, wherein said alkalinizing agent is ammonium hydroxide ($NH_4OH$) and said oxidizing agent is hydrogen peroxide ($H_2O_2$).

31. The method of claim 29, wherein said fluid comprises a solution of approximately 4 parts of water, approximately 1 part of 30% ammonium hydroxide ($NH_4OH$) and approximately 1 part of 30% hydrogen peroxide ($H_2O_2$).

* * * * *